United States Patent [19]

Kane et al.

[11] Patent Number: 4,476,221

[45] Date of Patent: Oct. 9, 1984

[54] PROTECTIVE SOLUTION FOR PRESERVING FUNCTIONAL CELLS

[75] Inventors: Odile B. Kane, Hoenheim; Eric George, Strasbourg; Chantal L. Tromp, Strasbourg; Serge Goll, Strasbourg, all of France

[73] Assignee: Centre Regional De Transfusion Sanguine, Strasbourg, France

[21] Appl. No.: 512,748

[22] Filed: Jul. 11, 1983

[30] Foreign Application Priority Data

Jul. 9, 1982 [FR] France ................ 82 12324
Mar. 16, 1983 [FR] France ................ 83 04426

[51] Int. Cl.$^3$ .................... A01N 1/02; A61K 35/18
[52] U.S. Cl. ........................ 435/2; 424/101; 435/240; 435/241
[58] Field of Search ............... 435/2, 240, 241; 424/101

[56] References Cited

U.S. PATENT DOCUMENTS 4,267,269  5/1981  Grode et al. ............... 435/2
4,356,172  10/1982  Nakao et al. ............... 435/2

OTHER PUBLICATIONS

Strauss–Chem. Abst., vol. 96 (1982), p. 205,391g.
Strauss–Chem. Abst., vol. 88 (1978), p. 60557p.

*Primary Examiner*—Sam Rosen
*Attorney, Agent, or Firm*—Young & Thompson

[57] ABSTRACT

A protective solution for the preservation of functional cells containing saccharose, and a phosphates buffer having a high concentration. The osmolarity of the solution is 330±10 mOsm and its pH 7.3±0.2. It can be mixed directly with red corpuscles of human or animal origin, with other blood cells such as leucocytes and platelets, and with cellular suspensions from various organs, either for their preservation for a long time, of the order of one week, in situ after thawing, or during transportation. The preferred composition is

| | |
|---|---|
| Adenine | 0.085 g ± 0.010 |
| Glucose | 5 g ± 0.5 |
| Saccharose | 47 g ± 2 |
| Monosodium phosphate monohydrate | 0.75 g ± 0.08 |
| Disodium phosphate dihydrate | 4 g ± 0.5 |
| Sodium chloride | 2.5 g ± 0.5 |
| Distilled water qsp | 1000 ml |

2 Claims, 5 Drawing Figures

PROTECTIVE SOLUTION FOR PRESERVING FUNCTIONAL CELLS

The invention covers the pharmaceutical, transfusional and biological engineering fields such as, for example, cellular cultures, and biological sciences.

The discovery which is the object of the present invention proposes preserving for cellular suspensions all their properties during in vitro preservation.

In the following description are used the following abbreviations:

| | |
|---|---|
| SAG | saline, adenine, glucose |
| SAG-MANNITOL | saline, adenine, glucose, mannitol |
| PAGG.S | phosphate, adenine, glucose, guanosine, saline |
| PAGGS-SORBITOL | phosphate, adenine, glucose, guanosine, saline, sorbitol |
| ATP | adenosine, triphosphate |
| 2,3-DPG | 2,3-diphosphoglycerate |
| Hb | hemoglobin |
| mg | milligram |
| µMOL/G/Hb | micromoles per gram of hemoglobin |
| Cr 51 | chromium 51 |
| CE | energy charge |

Models chosen for the examples are suspensions of human red corpuscles and in particular human red corpuscles that have been subjected to a freeze-thaw cycle, the cryoprotector employed during their freezing being glycerol of a final concentration of 17.4%.

Preservation solutions have been proposed for fresh cell suspensions. In the case of a suspension of fresh human red corpuscles, the following solutions have already been studied:
SAG
SAG-mannitol
PAGG.S
PAGGS-sorbitol.

These solutions permit good preservation of fresh red corpuscles. Applied to thawed red corpuscles taken as an example, they have, however, a very mediocre protective power which does not permit the preservation of all the qualities of the cells under study.

SAG and SAG-mannitol assure good energy balance (measure of ATP and energy charge) but, on the contrary, the functional balance becomes rapidly deficient (15% of 2,3-DPG by the fifth day).

The hemoglobin level, or free Hb is too high as early as the first day of preservation (value≧200 mg %).

PAGGS and PAGGS-sorbitol assure a better functional balance, but hematolysis is still too high (≧200 mg %) as early as the third day of preservation.

On the other hand a buffered saccharose solution has been proposed by Wolfdietrich Toursel for the preservation of thawed human red corpuscle suspensions. The medium was observed for 7 days and the results are as follows:

| Days | Free Hb x | S | ATP x | S | 2,3-DPG x | S |
|---|---|---|---|---|---|---|
| 0 | 34 | 9 | 3.5 | 0.6 | 14.8 | 1.3 |
| 1 | 41 | 8 | 3.4 | 0.4 | 13.6 | 1.1 |
| 2 | 48 | 8 | 3.2 | 0.8 | 12.1 | 2.1 |
| 3 | 60 | 11 | 2.6 | 0.5 | 8.4 | 3.2 |
| 7 | 104 | 19 | 1.7 | 0.6 | 2.1 | 0.8 |

If one accepts the limit of 2 µmol/g Hb which Dern assigns to ATP to ensure recirculation of 70% of the red corpuscles marked with Cr 51, 24 hours after transfusion, it will be seen that the preservation may not exceed three days. By contrast, at day 3, the 2,3-DPG still preserves a correct level.

Toursel also proposed three-day preservation of thawed red corpuscle suspensions protected with his medium.

The present invention has for its object to overcome these drawbacks of the existing solutions.

Thus it has for its object a protective solution for the preservation of functional cells, containing adenine, glucose, and a phosphates buffer, characterized in that it contains also saccharose, the phosphates buffer having a high concentration, the osmolarity of the solution being 330±10 mOsm and its pH 7.3±0.2.

The buffer strength of the solution is high and its constituents are mixed in non-toxic amounts.

After mixing the solution with thawed human red corpuscles, the following parameters have been observed:
the oxyphoric power of the thawed red corpuscle suspensions and their variation as a function of time, measured with 2,3-DPG.
the viability measured by:
 ATP
 energy charge
 free Hb level of the supernatant
 survival level of red corpuscles marked with Cr 51
 ammonium variation
 corpuscle strength The biological functions are all very well preserved as shown by the graphs of the accompanying drawings, in which.

Figure 1:
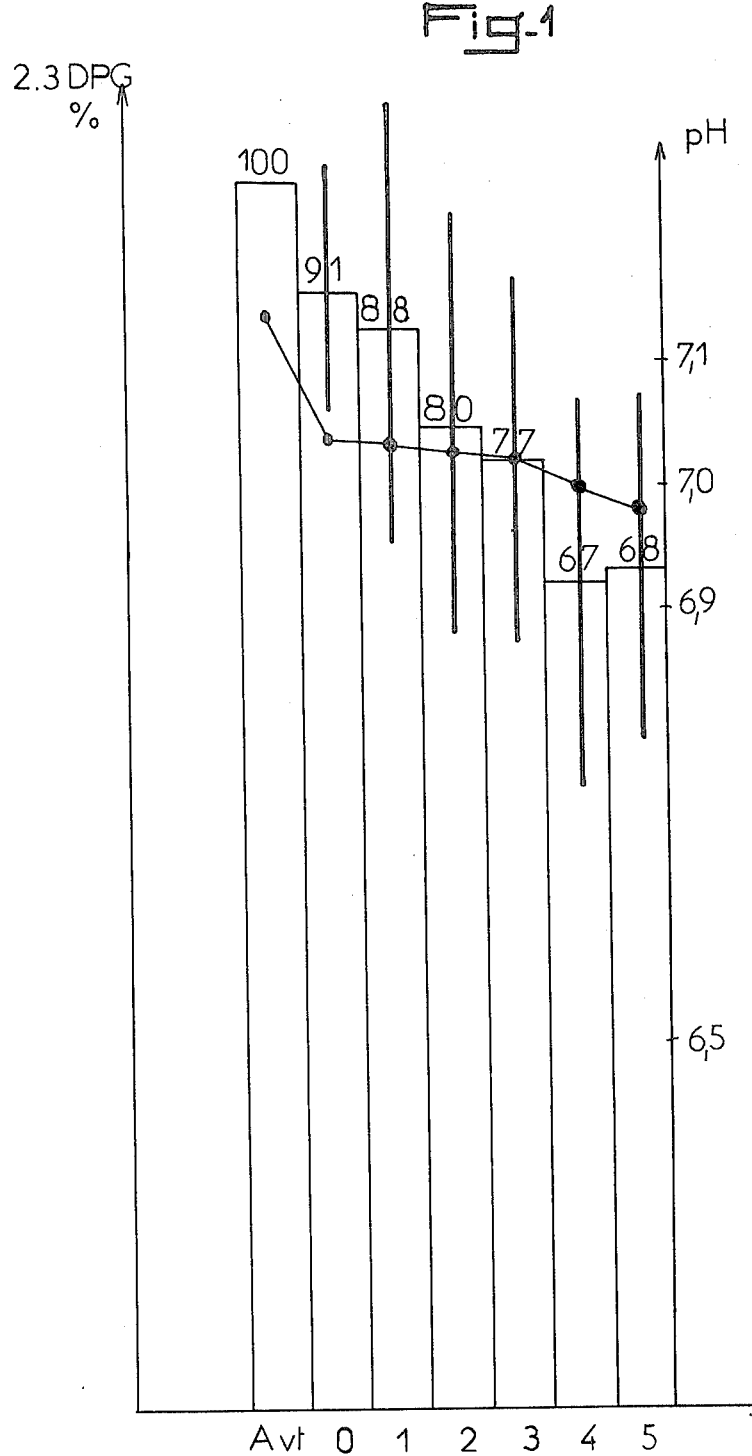
FIG. 1 shows the variation of 2,3-DPG and pH as a function of time.
Figure 2:
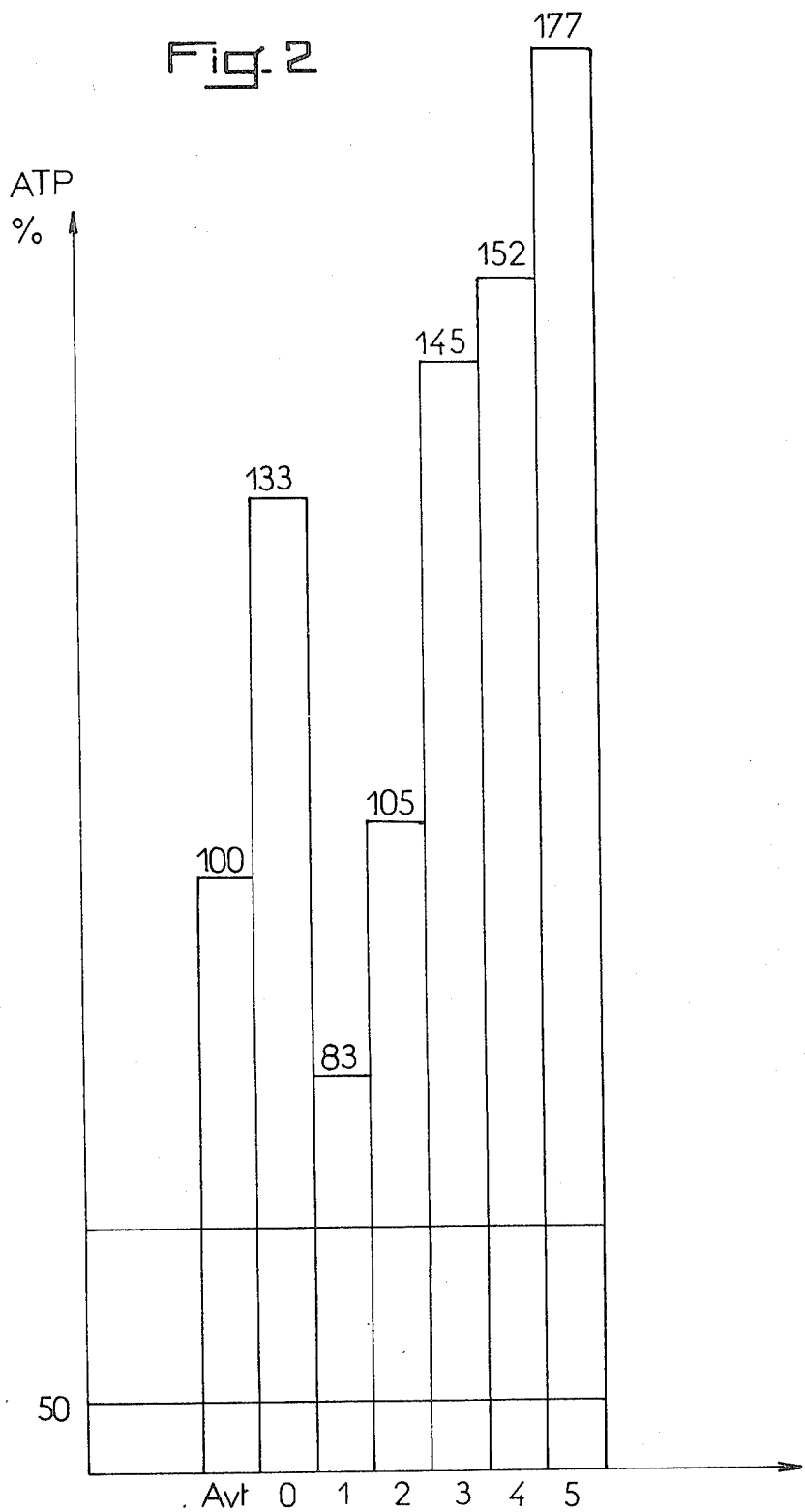
FIG. 2 shows the variation in the percentage of ATP as a function of time.
Figure 3:
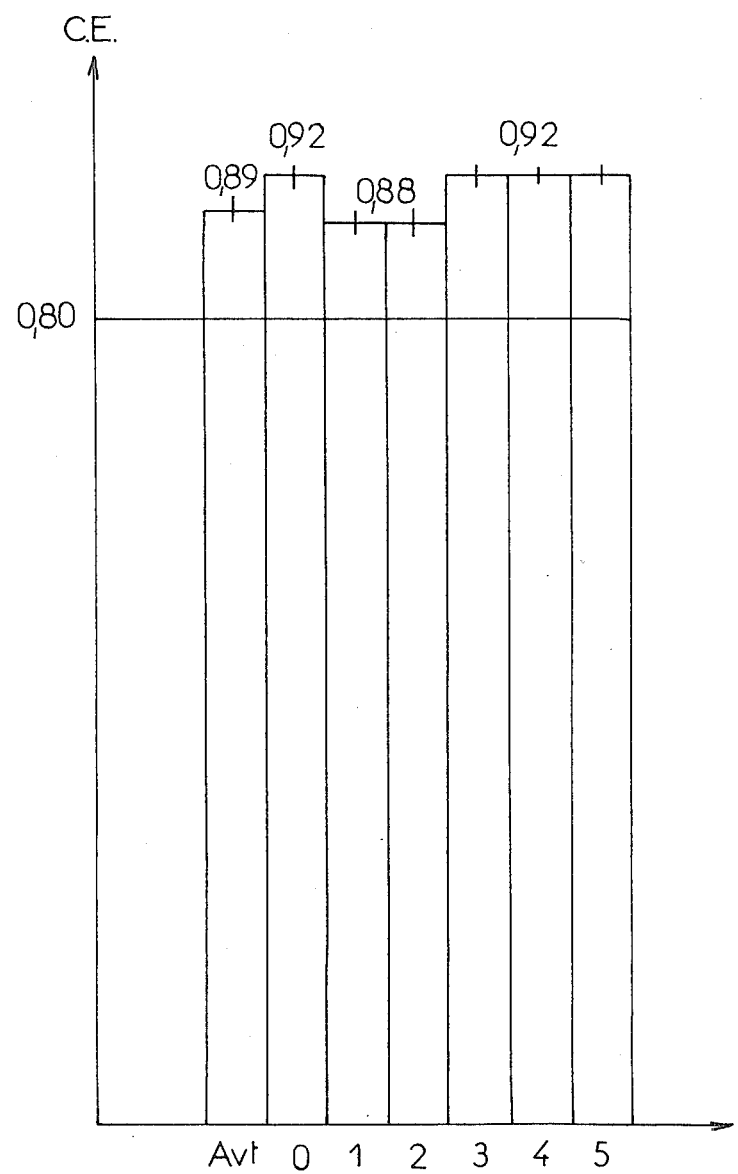
FIG. 3 shows the variation of the energy charge.

In FIGS. 1 to 3, the first column designated Avt represents fresh blood before freezing.

At day 5 the norms fixed by the Quality Control Commission of the National Society of Blood Transfusion for blood thawed at day 0 are broadly exeeded. At present the delay for the preservation of the thawed blood is at most 24 hours.

The solution according to the present invention, permits preservation at least one week for thawed blood taken as an example. This long preservation permits, in this case, deferred transfusion in the case of transport, bank support, or thawing in advance with a view toward scheduled operations. Simplified operation of the frozen blood bank will permit important economies in labor and cost.

All the histograms and curves concerning this work are presented in the accompanying drawings and show the high values of all the parameters observed before freezing and during five days after thawing.

The blood corpuscles are frozen by the technique of de Krijnen, preserved at −155° under gaseous hydrogen, thawed at +42° and washed in an automatic corpuscle washing machine.

At the end of washing, the frozen blood is present as concentrated corpuscles having a mean hematocrit of 78%. The red corpuscles are then suspended in a half volume of protective solution and the various quality controls are practiced each day except the measure of free Hb which is performed from day 1 on the supernatant after spontaneous sedimentation of the red corpuscles preserved at +4°.

Observation of the quality controls effectuated during the five days which follow freezing shows:

2,3-DPG very good concentration of this essential metabolite, which decreases only 30% relative to fresh blood by day 5 (FIG. 1).

Figure 4:
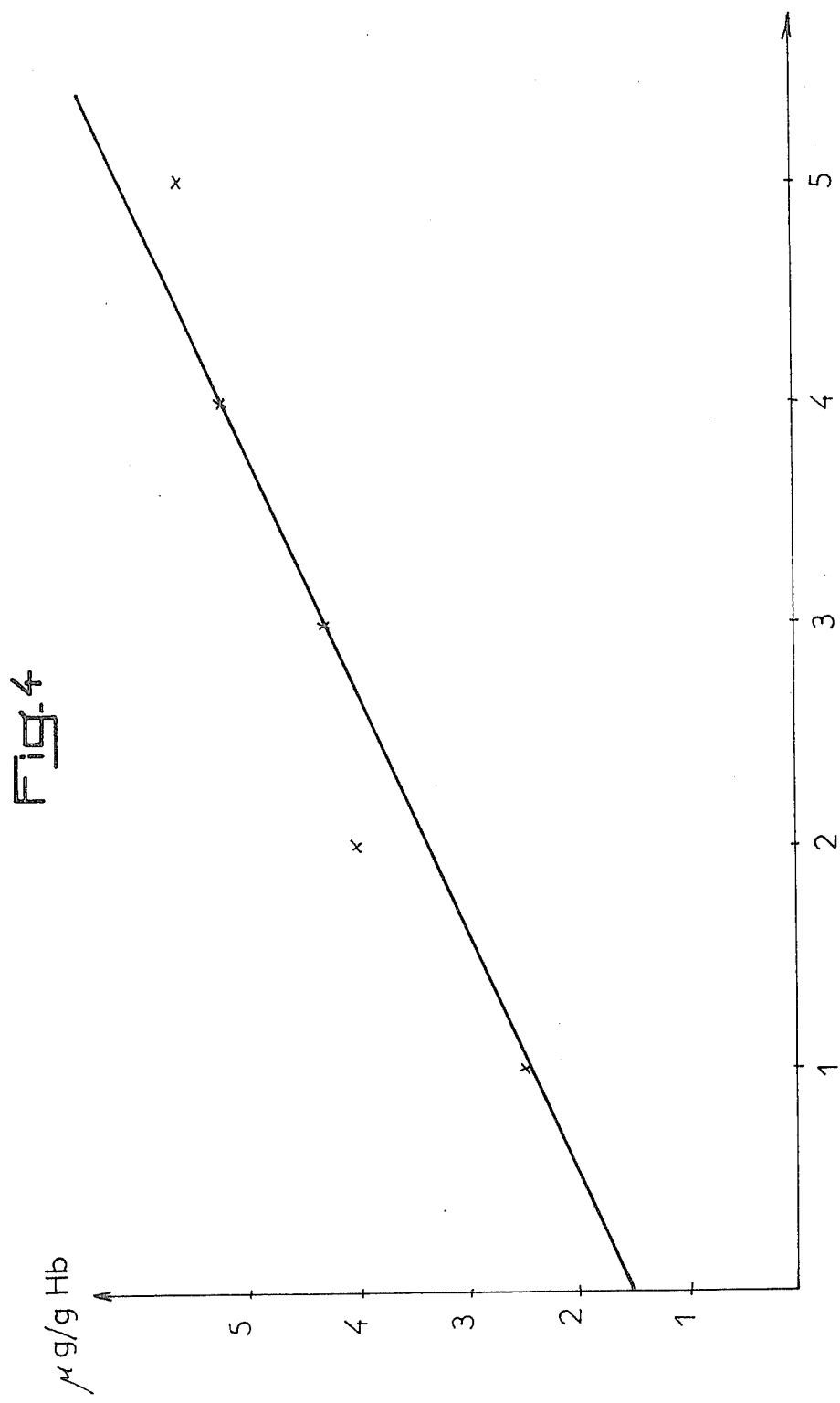
FIG. 4 shows the variation of ammonium.
Figure 5:
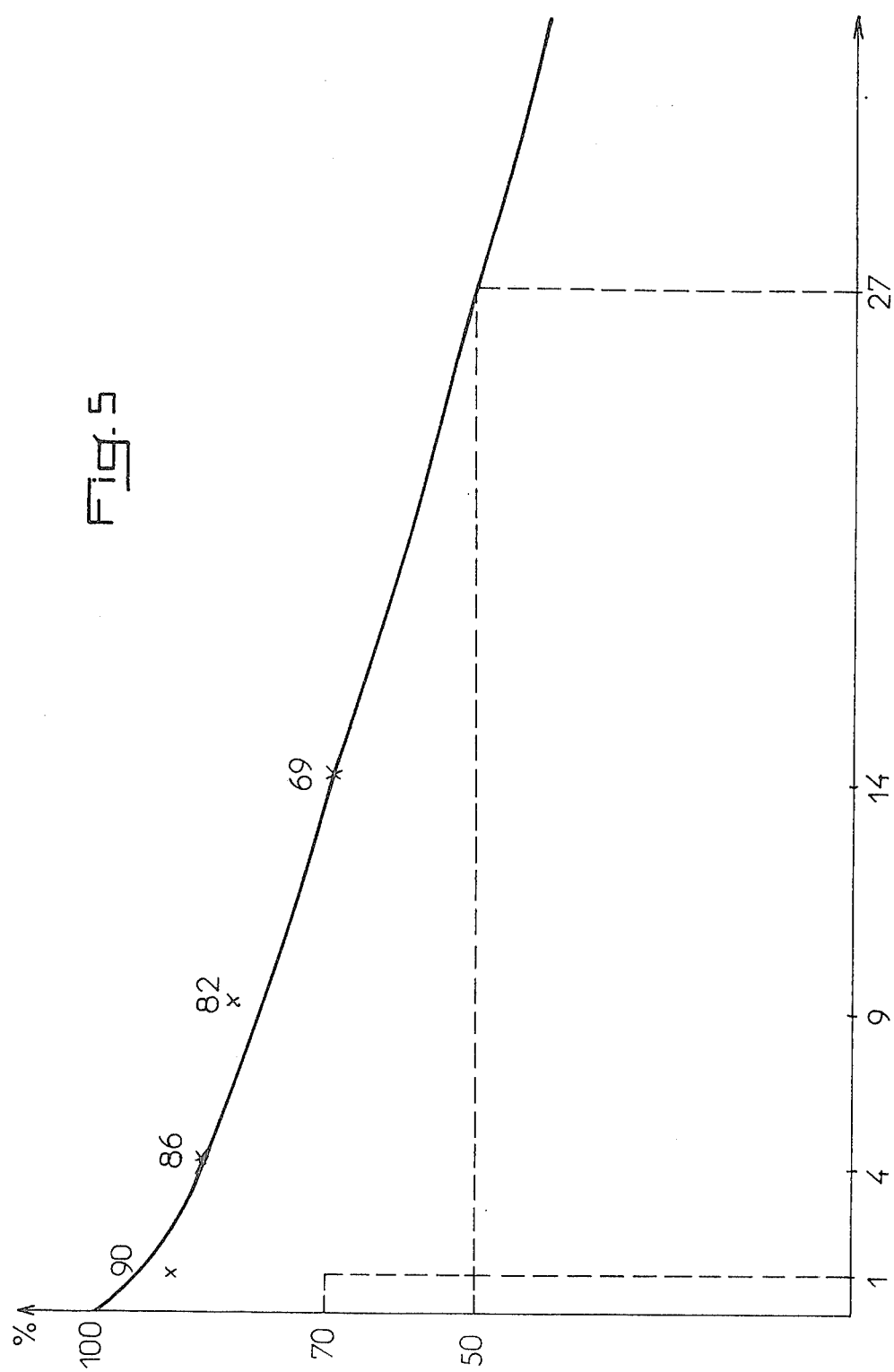
FIG. 5 shows the curve of the survival level of red corpuscles marked by chromium 51, three days after thawing.

ATP after a moderate drop at day 1, the ATP level rises regularly to a value of 177% of fresh blood at day 5 (FIG. 2).

energy charge: preserved in the given protective medium, the energy charge is remarkably stable and about 0.90, substantially like fresh blood (FIG. 3).

free hemoglobin also remains very stable for the duration of the study giving values four times less than the limiting level of 200 mg per unit.

the ammonium dosage shows low values at the 5th day, indicating very weak catabolism of the membrane proteins (FIG. 4).

overall resistance is increased.

radioisotope survival 24 hours after transfusion of red corpuscles marked with Cr 51 at the 3rd day of preservation shows values analogous to those of day 0, the half life is 27 days, which is a normal value (FIG. 5).

Whatever the freezing temperature and the storage temperature, the thawed erythrocite concentrates taken by way of example, whether preserved or not, must meet the criteria defined by the Quality Control Commission of the National Society of Blood Transfusion. These criteria have been compared with the found values.

at day 0 in plain thawed blood,
at day 5 in thawed blood protected by the solution of the present invention.

The following table shows that the found values remain substantially within the norms:

| corpuscle concentrate contains | official norms | thawed blood Day 0 | Day 5** |
| --- | --- | --- | --- |
| Total Hb | ≧34 g | 47.6 g | 47.5 g |
| Hematocrit | ≦80% | 75% | 60% |
| Total free Hb | ≦200 mg | 15 mg | 49 mg |
| Residual leucocytes | ≦1 × 10$^8$ | 0.6 × 10$^8$ | 0.2 × 10$^8$ |
| Sterility | Neg. | Neg. | Neg. |

** = with protective solution

Measurements taken at the 20th day showed:

free Hb levels of 154 mg per unit on the average, thus still below the level of 200 mg fixed by the official standards, ATP levels of 2.6 μmol/g. Hb on the average thus ensuring in principle the recirculation of 70% of the transfused red corpuscles.

It is certain that the proposed preservation solution ensures good protection of the thawed red corpuscles taken as an example, for one week.

According to a modified form of the invention, a solution adapted particularly for the preservation of thawed human red corpuscles advantageously has the following preferred composition:

| | |
| --- | --- |
| Adenine | 0.085 g ± 0.010 |
| Glucose | 5 g ± 2 |
| Saccharose | 47 g ± 2 |
| Monosodium phosphate monohydrate | 0.75 g ± 0.08 |
| Disodium phosphate dihydrate | 4 g ± 0.5 |
| Sodium chloride | 2.5 g ± 0.5 |
| Distilled water qsp | 1000 ml |
| The pH of the medium being equal to 7.40 ± 0.10 and its osmolarity being 320 ± 10 mOsm. | |

The different components are in the powdered state and are mixed in distilled water.

To this end, the preparation of such a solution comprises weighing separately on a precision balance the different components, then mixing them, introducing in a 1 lit. calibrated flask 0.9 lit. of distilled water and adding to it the powdered mixture, shaking the whole so as to effect rapid mixing, then placing on a water bath for two hours at a temperature of 37° C. to ensure complete dissolution of the powder, then adjusting the volume to 1 lit. by addition of distilled water, measuring the pH and the osmolarity, and finally filtering the solution through a sterile membrane.

The invention also has for its object a procedure for treating thawed, deglycerated and washed human red blood corpuscles. This process comprises, after thawing said red corpuscles in a water bath at 42° C. for 9 mins., effecting deglycerylation by manual predilution in a 1 lit. neutral glass bottle, by transfer tubes, simultaneously and over a period of 5 mins., thawed red corpuscles and 400 ml. of 3.5% chloride solution, and effecting washing of the obtained mixture by connecting the bottle to a tube of the washing chamber of an automatic corpuscle washer, the other tubes of the washing chamber being connected to 500 ml. bottles of 0.9% isotonic sodium chloride. The deglycerylated blood is introduced into the washing chamber and centrifuged at 3000 rpm for 3 mins., then the supernatant is eliminated by evacuation in a recovery chamber for the washing water. Three successive washings are thus effected with isotonic sodium chloride, by automatically introducing to each washing, 500 ml. of solution in the washing chamber and effecting bubbling for a period of 100 seconds followed by centrifugation of the mixture at 3000 rpm for 90 seconds and evacuation of the supernatant in the recovery chamber, the red corpuscles remaining in the washing chamber in the form of an erythrocyte concentrate. The last washing is followed by centrifugation at 3000 rpm for 3 mins. so as to obtain a hematocrit of 85%. The obtained washed erythrocyte concentrate is introduced in a plastic bag or the like, for transfusional use, by means of the transfer tube of the latter, then the bag is weighed and the volume of concentrate is noted.

This erythrocyte concentrate is then treated according to a treatment process which is also an object of the invention. This process consists in subjecting the bag of concentrate to constant gentle agitation on the plate of an agitator of platelet concentrates, or the like, and in adding a half volume of protective solution by means of the transfer tube of the bag, for 10 mins., the transfer tube then being welded at 2 cm., 2.5 cm. and 3 cm. from the bag with the help of a special welder for medical plastic tubing. This agitation of the bag is then continued for 20 mins. to obtain blood ready for use, which may be stocked in a refrigerated cabinet or transmitted under conditions of refrigeration at 4° C.

When maintained at a temperature strictly of 4° C., the transfusional qualities of the thawed blood thus preserved are ensured for 12 days with absolute assurance for 9 days, whereas under existing conditions this delay cannot exceed in any case 3 days, more frequently 24 hours.

Of course, the invention is not limited to the described embodiments. Modifications are possible, particularly as to the constituents of the solution and their concentration, without thereby departing from the scope of protection of the invention.

We claim:

1. Protective solution for the preservation of thawed human red corpuscles, having the following composition:

| | |
|---|---|
| Adenine | 0.085 g ± 0.010 |
| Glucose | 5 g ± 0.5 |
| Saccharose | 47 g ± 2 |
| Monosodium phosphate monohydrate | 0.75 g ± 0.08 |
| Disodium phosphate dihydrate | 4 g ± 0.5 |
| Sodium chloride | 2.5 g ± 0.5 |
| Distilled water qsp | 1000 ml | the pH of the medium being equal to 7.40±0.10 and its osmolarity 320±10 mOsm.

2. Process for the treatment of thawed human red corpuscles comprising, after thawing said red corpuscles over a water bath at 42° C. for 9 mins., and washing the mixture obtained in an automatic corpuscle washer whose program is regulated to obtain a mean hematocrit of 85% at the end of washing, followed by the introduction of the washed erythrocyte concentrate obtained in a plastic bag or the like, for transfusional use, by means of the transfer tubing of this latter, the bag being weighed and its volume of concentrate recorded, subjecting the bag to constant gentle agitation on the plate of an agitator for platelet concentrates, then adding, by means of the transfer tube of the bag, over 10 mins., a half volume of protective solution as in claim 1, welding the transfer tubing at 2 cm., 2.5 cm. and 3 cm. from the bag with the aid of a welder for medical plastic tubing, and finally continuing the agitation of the bag for 20 mins. to obtain blood ready for use which can be stored in a refrigerated cabinet or transported under refrigeration at 4° C.

* * * * *